US011253800B2

(12) United States Patent
Sebastian

(10) Patent No.: US 11,253,800 B2
(45) Date of Patent: Feb. 22, 2022

(54) PLATE FOR A FILTER PRESS, FILTER PRESS, USE OF THE FILTER PRESS AND METHOD FOR CLEANING THE FILTER PRESS

(71) Applicant: STRASSBURGER FILTER GMBH & CO. KG, Westhofen (DE)

(72) Inventor: Jürgen Sebastian, Westhofen (DE)

(73) Assignee: STRASSBURGER FILTER GMBH & CO. KG, Westhofen (DE)

(*) Notice: Subject to any disclaimer, the term of this patent is extended or adjusted under 35 U.S.C. 154(b) by 396 days.

(21) Appl. No.: 15/969,936

(22) Filed: May 3, 2018

(65) Prior Publication Data

US 2018/0318731 A1  Nov. 8, 2018

(30) Foreign Application Priority Data

May 4, 2017 (DE) ............. 10 2017 207 484.1

(51) Int. Cl.
*B01D 25/32* (2006.01)
*B01D 25/12* (2006.01)
(Continued)

(52) U.S. Cl.
CPC ............ *B01D 25/32* (2013.01); *A61J 3/00* (2013.01); *A61M 1/3496* (2013.01);
(Continued)

(58) Field of Classification Search
CPC .............. A61J 3/00; A61M 1/3496; A61M 2202/0415; B01D 2201/342;
(Continued)

(56) References Cited

U.S. PATENT DOCUMENTS 4,210,516 A * 7/1980 Mose .................. C25B 9/04
204/284
4,431,502 A * 2/1984 Ford .................. C25B 9/00
204/252

(Continued)

FOREIGN PATENT DOCUMENTS

CN   102343168 A   2/2012
CN   106139661 A   4/2015
(Continued)

OTHER PUBLICATIONS

H. Gasper, Handbuch der industriellen Fest/Flüssig-Filtration, 1990, pp. 104-111, ISBN 3-7785-1874-8, Hüthig Buch Verlag GmbH, Heidelberg.

(Continued)

*Primary Examiner* — Dirk R Bass
(74) *Attorney, Agent, or Firm* — Hudak, Shunk & Farine Co. LPA

(57) ABSTRACT

A plate for a filter press, a filter press, the use of such a filter press as well as a method of cleaning and sterilization of such a filter press. The plate for a filter press has a base body, consisting of a first material with a hardness $H_1$ and having an outer circumferential surface, and a frame arranged on the outer circumferential surface, consisting of a second material with a hardness $H_2$, where $H_2<H_1$, and wherein the frame has on at least one side surface at least one encircling seal protruding relative to the side surface.

18 Claims, 9 Drawing Sheets

(51) Int. Cl.
*B01D 25/21* (2006.01)
*B01D 41/04* (2006.01)
*A61J 3/00* (2006.01)
*A61M 1/34* (2006.01)
*B01D 25/164* (2006.01)
*B01D 25/28* (2006.01)

(52) U.S. Cl.
CPC ........... *B01D 25/12* (2013.01); *B01D 25/164* (2013.01); *B01D 25/215* (2013.01); *B01D 25/285* (2013.01); *B01D 41/04* (2013.01); *A61M 2202/0415* (2013.01); *B01D 2201/342* (2013.01); *B01D 2201/345* (2013.01)

(58) Field of Classification Search
CPC ............. B01D 2201/345; B01D 25/12; B01D 25/164; B01D 25/215; B01D 25/285; B01D 25/32; B01D 41/04
See application file for complete search history.

(56) References Cited

U.S. PATENT DOCUMENTS

| | | | | |
|---|---|---|---|---|
| 4,488,946 A | * | 12/1984 | Morris | ...................... C25B 9/77 |
| | | | | 205/338 |
| 4,915,803 A | * | 4/1990 | Morris | ...................... C25B 9/20 |
| | | | | 204/252 |

FOREIGN PATENT DOCUMENTS

| | | |
|---|---|---|
| DE | 10221061 A1 | 11/2003 |
| DE | 102012209591 A1 | 12/2013 |
| WO | 2006015637 A1 | 2/2006 |

OTHER PUBLICATIONS

First Office Action for Chinese family member application No. 201810398886.8 dated Mar. 29, 2021.
Chinese Search Report for Chinese family member application No. 201810398886.8 dated Mar. 5, 2021.

\* cited by examiner

PLATE FOR A FILTER PRESS, FILTER PRESS, USE OF THE FILTER PRESS AND METHOD FOR CLEANING THE FILTER PRESS

FIELD OF THE INVENTION

The present invention relates to a plate for a filter press, a filter press, the use of such a filter press as well as a method of cleaning and sterilization of such a filter press.

BACKGROUND OF THE INVENTION

Filter presses are divided into so-called frame filter presses, chamber filter presses and membrane filter presses. They involve the identical design of the filter press frame, but outfitted with different kinds of plates (see, e.g., Horst Gasper "Handbuch der industriellen Fest/Flüssig-Filtration", Hüthig-Verlag Heidelberg 1990, p. 104-111).

Filter presses find use chiefly in the food and beverage industry, as well as in cosmetics, chemistry and the pharmaceutical industry. Especially in the pharmaceutical industry, the highest purity requirements and a proper GMP (Good Manufacturing Practice) design are demanded of the filtration systems. GMP involves quality demands which must be met during the manufacturing, processing, packaging and storage of pharmaceuticals.

DE 102 21 061 A1 discloses a plate arrangement in which filter plates and membrane plates are arranged alternately. The filter plate is provided on both side surfaces with a filter cloth, which is secured in a recess of the base body of the filter plate. The membrane plate has a membrane on both sides, which is secured in a recess on either side of the base body of the membrane plate.

In the filter press, a filter chamber is formed between the filter cloth of the filter plate and the adjacent membrane of a membrane plate. A pressure chamber is formed between the membrane and the base body of the membrane plate. A further filter cloth may be placed on top of the membrane plate on either side when the filter press is assembled.

The filter cloths each extend as far as the margin of the filter and membrane plates and are pressed against each other there when the filter press is closed and are held in this manner. Because the filter cloths end at the margin of the plates, there is a risk of liquid dripping out from this area, unless additional sealing elements are provided.

In order to clean the filter press, the filter press is opened and the filter cakes are extracted at the bottom. The individual filter and membrane plates are removed and cleaned in a cleaning device located outside the filter press. Upon opening the filter press, the filter cloths may be taken out separately and cleaned.

When filter beds are used in place of filter cloths, the filter beds must be disposed of and replaced with new filter beds.

From WO 2006/015637 A1 there is known a filter device with a predetermined number of filter and cake frames with a sealing device. The filter and cake frames are arranged in an alternating sequence, wherein the filter frames have a filter means at least on their side facing the respective cake frame, which can be secured at the margin in clamping gaps between two respective adjacent frames.

A connection space is situated between the sealing device and the clamping gap, which emerges into a central connection channel, making possible the supply and drainage of cleaning media.

The cleaning procedure for this filter device calls for first opening the clamping gap and removing the filter medium through the clamping gap. After this, the plates are once more pressed together tightly and the filter device is operated accordingly in a cleaning mode, similar to the filter mode, making use of cleaning media and/or rinsing media and/or sterilization media.

After the cleaning procedure, the filter press must be opened once more so that fresh filter media can be inserted. This may result in a contamination of the interior with dirt particles.

Increasingly often, filter media in the form of filter cloths are being used, which can be reused up to 100 times after a cleaning.

DE 10 2012 209 591 A1 therefore describes a filter press with a plate arrangement consisting of membrane plates, filter plates and frame plates, wherein filter cloths are fastened removably by means of support elements in the form of retaining pins in the marginal areas of the side surfaces of membrane and filter plates.

In this way, the reusable filter cloths can remain in the cleaning device on the membrane plates or the filter plates during the cleaning and do not have to be removed prior to the cleaning, as in the above described documents.

SUMMARY OF THE INVENTION

The problem which the present invention proposes to solve is to provide a plate for a filter press, a filter press, and a method for cleaning and/or sterilization, making it possible to perform a cleaning of the filter press and its components which meets the high quality standards, especially in the pharmaceutical industry, and which enables an easy cleaning and sterilization of all areas that come into contact with the filtered product.

This problem is solved with a plate for a filter press, a filter press, and the use of a filter press as well as a method for cleaning and/or sterilization of a filter press.

The plate for the filter press includes a base body, consisting of a first material with a hardness $H_1$ and having an outer circumferential surface, and a frame arranged on the outer circumferential surface, consisting of a second material with a hardness $H_2$, where $H_2<H_1$, and wherein the frame has on at least one side surface at least one encircling seal protruding relative to the side surface.

The filter plate has a plurality of plates arranged parallel to each other, wherein at least every second plate is a plate described above. The filter press is used for the filtration of blood plasma or for the manufacturing of pharmaceutical products.

A method for cleaning the plates of a filter press is disclosed and involves the following steps:
(a) a first compressing of the plates, wherein only the second protrusion of the seal is compressed,
(b) at least one rinsing procedure with a cleaning, rinsing and/or sterilization medium and
(c) a second compressing of the plates, wherein both the second and also the first protrusion of the seal are entirely compressed.

A method for cleaning the plates of a filter press is disclosed, wherein the following steps are performed in advance of steps (a), (b) and (c):
(1) sliding apart the plate arrangement,
(2) removal of the filter cake,
(3) removal of the plates and separate cleaning
(4) installing of the cleaned plates.

The plate for a filter press is characterized by a base body, consisting of a first material with a hardness $H_1$ and having an outer circumferential surface, and a frame arranged on the outer circumferential surface, consisting of a second material with a hardness $H_2$, where $H_2<H_1$, and wherein the frame has on at least one side surface at least one encircling seal protruding relative to the side surface.

The use of two different hard materials for different regions of the plate has the advantage that the materials can be optimally adjusted in regard to their properties for the filtration region on the one hand and the sealing region on the other hand. The base body is subjected to high pressures during the filtration, so that the base body can be made from hard and therefore stable material. The frame is made of softer material, which provides the necessary sealing function when the plates are pressed together, on account of its flexibility.

It is thus possible to fabricate the peripheral seal, which protrudes relative to the side surface on at least one side surface of the frame, from the same material as the frame.

In one advantageous embodiment, the seal and the frame are made from a single piece.

On account of the high purity and quality demands, joints and sharp edges or gaps should be avoided. The fabrication of the frame and the seal from a single piece, as well as the interconnection of base body and flexible frame therefore prevents the occurrence of production-related joints, edges and/or leaks where contaminants may accumulate during the use of the plate in a filter press and which are very hard to reach, if at all, during a cleaning procedure.

Preferably the frame is joined by its inner circumferential surface to the outer circumferential surface of the base body.

In one preferred embodiment, the inner circumferential surface of the frame is welded to the outer circumferential surface of the base body.

As compared to other joining methods for plastics, such as mechanical joining or gluing, welding offers the advantage of a high connection quality and tightness to liquid media.

Especially when the base body of the plate consists of polypropylene, a welded connection with a thermoplastic elastomer based on polypropylene is advantageous, since it is easier to form a mutual joint between the two components.

Preferably the frame has a hardness of 90 to 100 shore A, preferably 93 to 95 shore A.

Advantageously, the frame has a thermoplastic elastomer or consists entirely of the thermoplastic polymer.

Thermoplastic elastomers are plastics which usually consist of a "soft" elastomer such as ethylene-propylene-diene; M group (EPDM), and a hard thermoplastic component such as polypropylene.

One advantage of these plastics is their reversible shape change, on the one hand, and the possibility of welding them on the other hand, in order to produce water-tight connections.

With the aforementioned hardness, the flexible frame is softer than the base body, which preferably consists of polypropylene. Preferably the base body has a hardness $H_1$ of 60 to 80 shore D. The hardness measurement is done according to the standard DIN ISO 7619-1.

Preferably the encircling seal in the unloaded condition has a first protrusion which passes into a second protrusion.

Preferably the second protrusion extends beyond the first protrusion.

Such a stepped seal has the advantage that, when a plate arrangement is pressed together in a filter press, a defined intermediate position of the plates relative to each other can be produced. This defined intermediate position is used in the installed state preferably for the sterilization of the plates.

Preferably every second plate of the plate arrangement has the construction according to the invention of a base body and a frame with seal.

In the cleaning state and in the filter state, the plates are subjected to different pressing forces according to the invention. Whereas in the filter state the pressing force of 240 bar, for example, is so large that the flexible seal is compressed in its entirety and the plates lie firmly against each other, the pressure for the cleaning state is chosen such that the flexible seal is only compressed enough for the adjacent plate to reach the first protrusion and thus a narrow gap of a few millimeters is produced between adjacent plates, which is wide enough to perform a so-called CIP (Cleaning in Place) procedure. The CIP procedure is a known method involving a cleaning of the filter press in situ, during which the filter press is operated with a cleaning and/or sterilization medium in place of the filtering medium, as described in the aforementioned document WO 2006/015637 A1.

Preferably the first protrusion has an abutment surface oriented parallel to the side surface of the frame.

Such a parallel surface has the advantage that a definite intermediate position can be achieved during the compressing and the starting pressure is distributed evenly over the entire plate arrangement. In this way, a propagation of the pressure across the entire plate arrangement is assured. If the first protrusions of the plates were not designed as an end stop, the seals of the first plates to which the pressing force is applied would be deformed more heavily, i.e., pressed beyond the intermediate position, while the seals of the plates at the other end of the filter press might not even be deformed.

Usually a filter press has a plate arrangement with up to 120 filter plates (e.g., 28 membrane plates, 29 filter plates, 56 frame plates). The steplike seal ensures that the pressing force applied for the cleaning is evenly distributed over the entire plate arrangement and a definite gap of a few millimeters is produced between all adjacent plates, which is necessary for the cleaning.

An abutment surface of the first protrusion running parallel to the side surface of the plate confers a greater resistance to deformation on it and enables an optimized pressure propagation over the entire plate arrangement as well as the determination of a pressure necessary to generate the intended gap width. Advantageously, the desired gap width corresponds to the height of the first protrusion, which is usually around 1.5 mm. Thanks to the abutment surface of the first protrusion oriented parallel to the side surface, large material stresses in the seal are avoided and a longer service life of the seal is assured.

Preferably the first protrusion is arranged closer to the outer circumferential surface of the frame than the second protrusion.

Thanks to the arrangement of the first protrusion closer to the outer circumferential surface of the frame than the second protrusion, it is ensured that the larger protrusion bounds off the inner chamber region and no joint is created which would be hard for the cleaning and/or sterilization medium to reach.

Advantageously the side surface having the seal has an encircling groove, and the groove is preferably adjacent to the second protrusion. Preferably the groove is immediately bordering on the second protrusion, which means that the flank of the second protrusion passes into the groove flank.

Preferably the groove has a depth of 0.5 to 1.5 cm and especially preferably 0.8 to 1.2 cm as well as a width of 10-20 mm.

The groove width is measured in the plane of the side surface.

A groove immediately bordering on the second protrusion makes it possible to take up the displaced volume of the compressed seal and thus reduces the resulting material stresses in the compressed state and therefore increases the lifetime of the seal. The groove volume should therefore be coordinated with the volume of the seal.

The sequence of first and second protrusion may also be interchanged.

In one advantageous embodiment, the plate is a filter plate.

In another advantageous embodiment, the plate is a membrane plate.

In one especially preferred embodiment, the plate is a frame plate.

For the solution of the problem, each of the aforementioned plates of a filter press may be designed as a plate according to the invention. In particular, the design of the plate according to the invention as a filter frame is preferable, since this can be manufactured with the least effort and the lowest cost and consequently is easily and cheaply replaced in event of its failure.

Advantageously the frame has at least one through borehole for the supply and drainage of cleaning agent and at least one through borehole for venting. The through boreholes extend preferably perpendicular to the plane of the plate through the frame.

Preferably the through boreholes are situated in the encircling groove.

The arrangement of a through borehole in the frame and especially in the encircling groove enables the supply and the drainage of cleaning, rinsing and or sterilizing means especially at the critical cleaning location of the seal and in the pressing region of neighboring plates.

The invention furthermore relates to a filter press with a plurality of plates arranged parallel to each other, wherein at least every second plate is a plate of the above described kind.

The use of the filter press is intended in particular for the filtration of blood plasma or for the manufacturing of pharmaceutical products, since the filter press thanks to the use of the plates according to the invention meets the highest quality standards in terms of cleaning and sterilization.

Furthermore, the invention relates to a method for the sterilization of a filter press according to the invention as described above.

The method proposes the following steps:

A method for cleaning the plates of a filter press is disclosed, involving the following steps:
 (a) a first compressing of the plates, wherein only the second protrusion of the seal is compressed,
 (b) at least one rinsing procedure with a cleaning, rinsing and/or sterilization medium and
 (c) a second compressing of the plates, wherein both the second and also the first protrusion of the seal are entirely compressed.

With this cleaning procedure, all product-contacting regions are cleaned and/or sterilized. Preferably the filter press after performing the cleaning procedure will no longer be opened until the filtration. After a sterilization, the sterilization liquid preferably remains in the filter press, until the filtration operation is commenced.

Preferably the method for cleaning the plates of a filter press involves the following steps:
 (1) sliding apart the plate arrangement,
 (2) removal of the filter cake,
 (3) removal of the plates and separate cleaning
 (4) installing of the cleaned plates
   (a) a first compressing of the plates, wherein only the second protrusion of the seal is compressed,
   (b) at least one rinsing procedure with a cleaning, rinsing and/or sterilization medium and
   (c) a second compressing of the plates, wherein both the second and also the first protrusion of the seal are entirely compressed.

The method of the invention for cleaning a filter press proposes that, after a completed filter process, the plates of the filter press are pushed apart enough so that the filter cake can be detached. Next, the plates are individually removed and cleaned separately. After replacing all plates in the filter press, they are once more pressed together—the first compressing—until the plates meet at the abutment surface of the first protrusion of the encircling seal of the respective adjacent plate and a gap is produced corresponding just to the height of the first protrusion.

After this, the filter press is operated in a way comparable to the filter mode in the cleaning mode with the use of cleaning, rinsing and/or sterilization media, the cleaning, rinsing and/or sterilization medium being supplied to and drained from the chamber space located in the plates by means of at least one through borehole in the margin of the plates. After the rinsing mode, the plates are pressed together—the second compressing—such that both the first and the second protrusion of the seal are fully compressed and the filter press is ready for a new filtration process.

BRIEF DESCRIPTION OF THE DRAWINGS

Sample embodiments of the invention shall be explained more closely below with the aid of the figures.

DETAILED DESCRIPTION OF THE INVENTION

Figure 1:
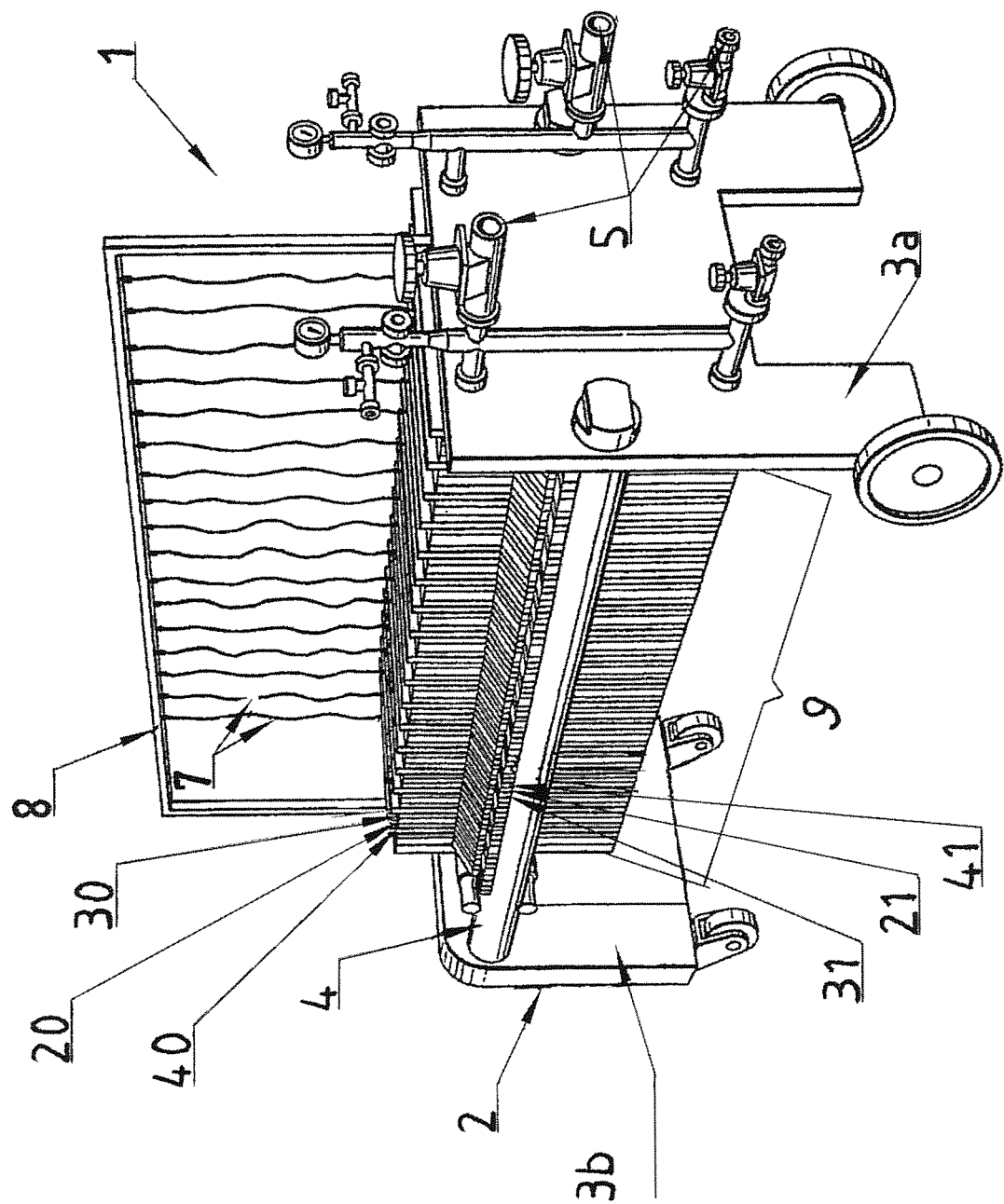
FIG. 1 shows a perspective representation of a filter press.

FIG. 1 shows a filter press 1 in perspective view. The filter press 1 has a mobile frame 2, having at either end a frame plate 3a, 3b, which are joined together by two support beams 4. On these support beams 4 there are hung the frame plates 20, membrane plates 30 and filter plates 40 by their retaining tabs 21, 31, 41 in a predetermined sequence to form a plate arrangement 9, being pressed against each other tightly by a pressing device. The membrane plates 30 have pressurized air ports 7', to which hoses 7 are fastened, being led by a rod 8 to a common pressurized air supply (not shown).

Figure 3:
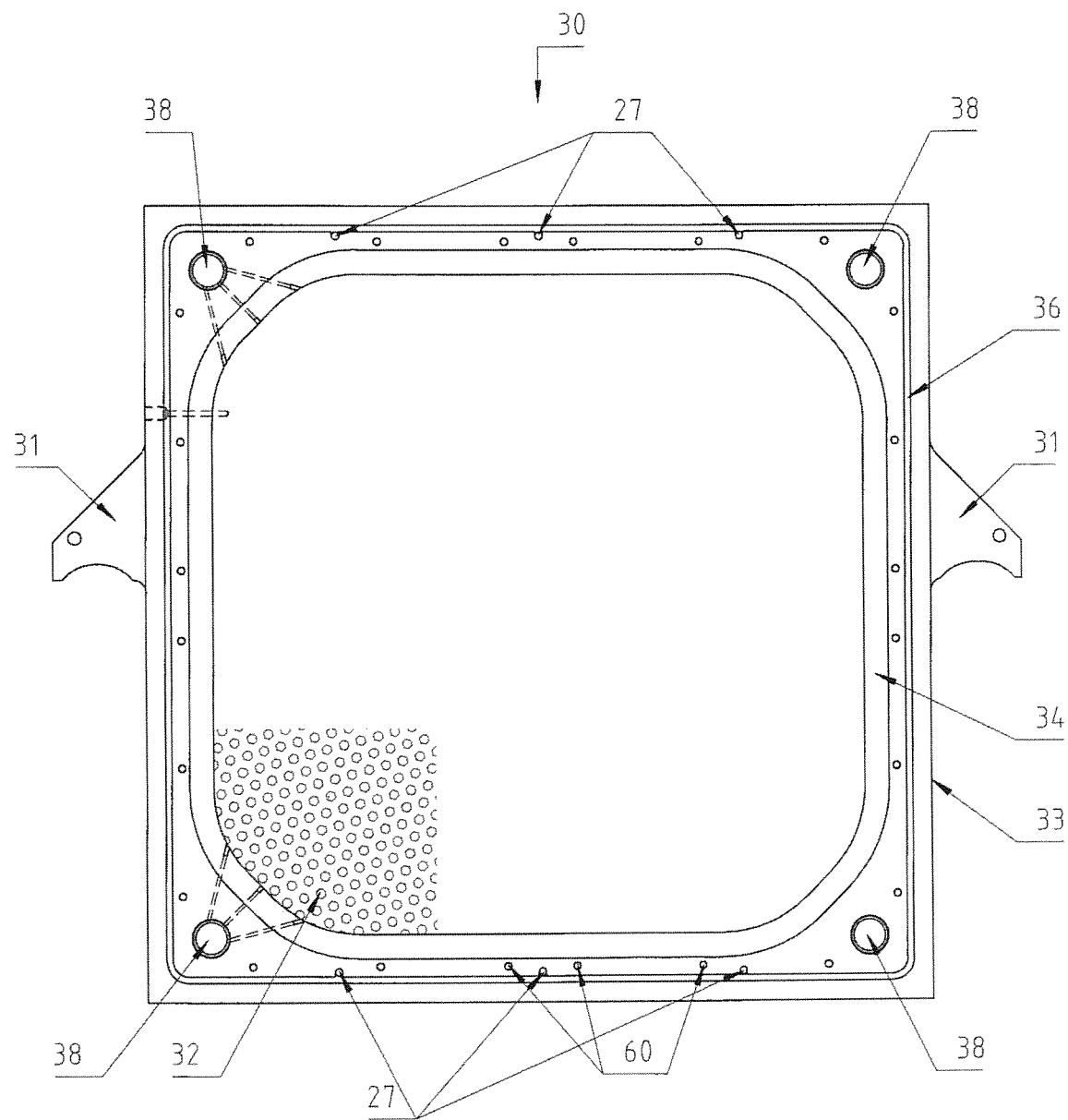
FIG. 3 shows a top view of a membrane plate known in the prior art.
Figure 4:
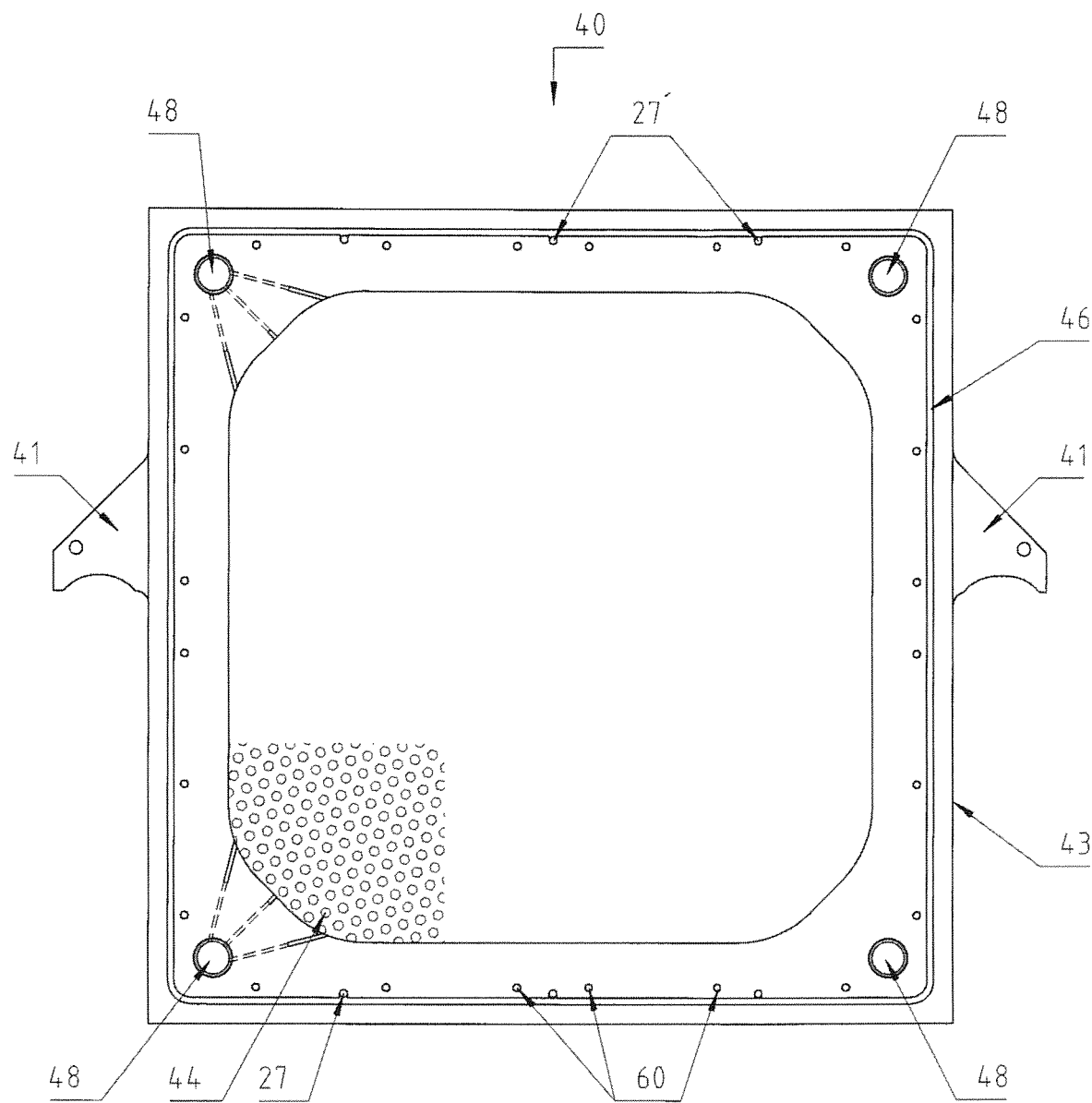
FIG. 4 shows a top view of a filter plate known in the prior art.
Figure 8:
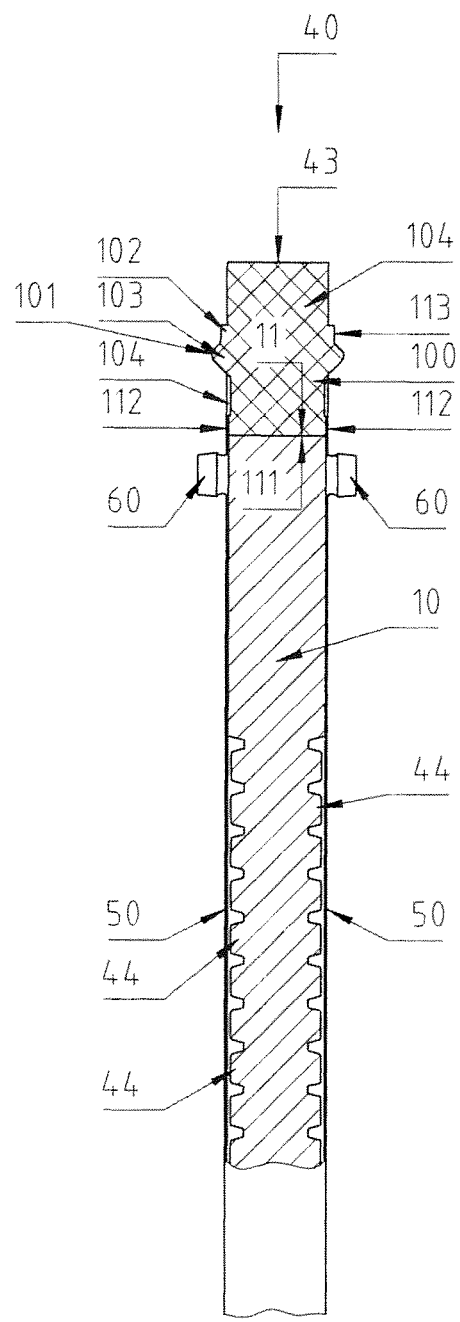
FIG. 8 shows a partial cross section through a filter plate according to the invention.
Figure 9:
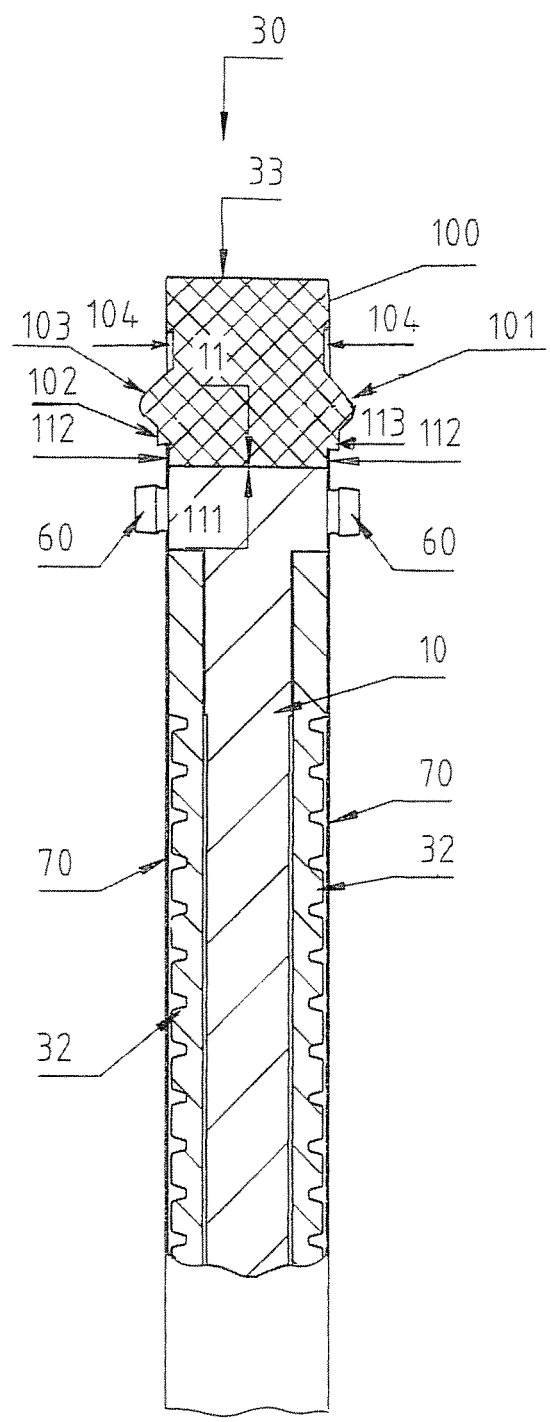
FIG. 9 shows a partial cross section through a membrane plate according to the invention.

In the front part of the frame there are several connections 5 for nonfiltrate supply and filtrate drainage, being connected to filtrate and nonfiltrate channels situated inside the plate arrangement 9. In order to form these filtrate and nonfiltrate channels, appropriately dimensioned eyelets 28, 38, 48 are provided in the plates 20, 30 and 40 in the corner regions, being indicated in FIGS. 2, 3 and 4 for the aforementioned kinds of plates. The membrane plates and filter [plates] represented in FIGS. 3 and 4 are plates of the prior art, which are assembled together with the frame plates 20 according to the invention. FIGS. 8 and 9 show membrane and filter plates 30, 40 according to the design of the invention, which can be assembled with conventional frame plates, or frame plates without the seal according to the invention, to make a plate arrangement.

Figure 2:
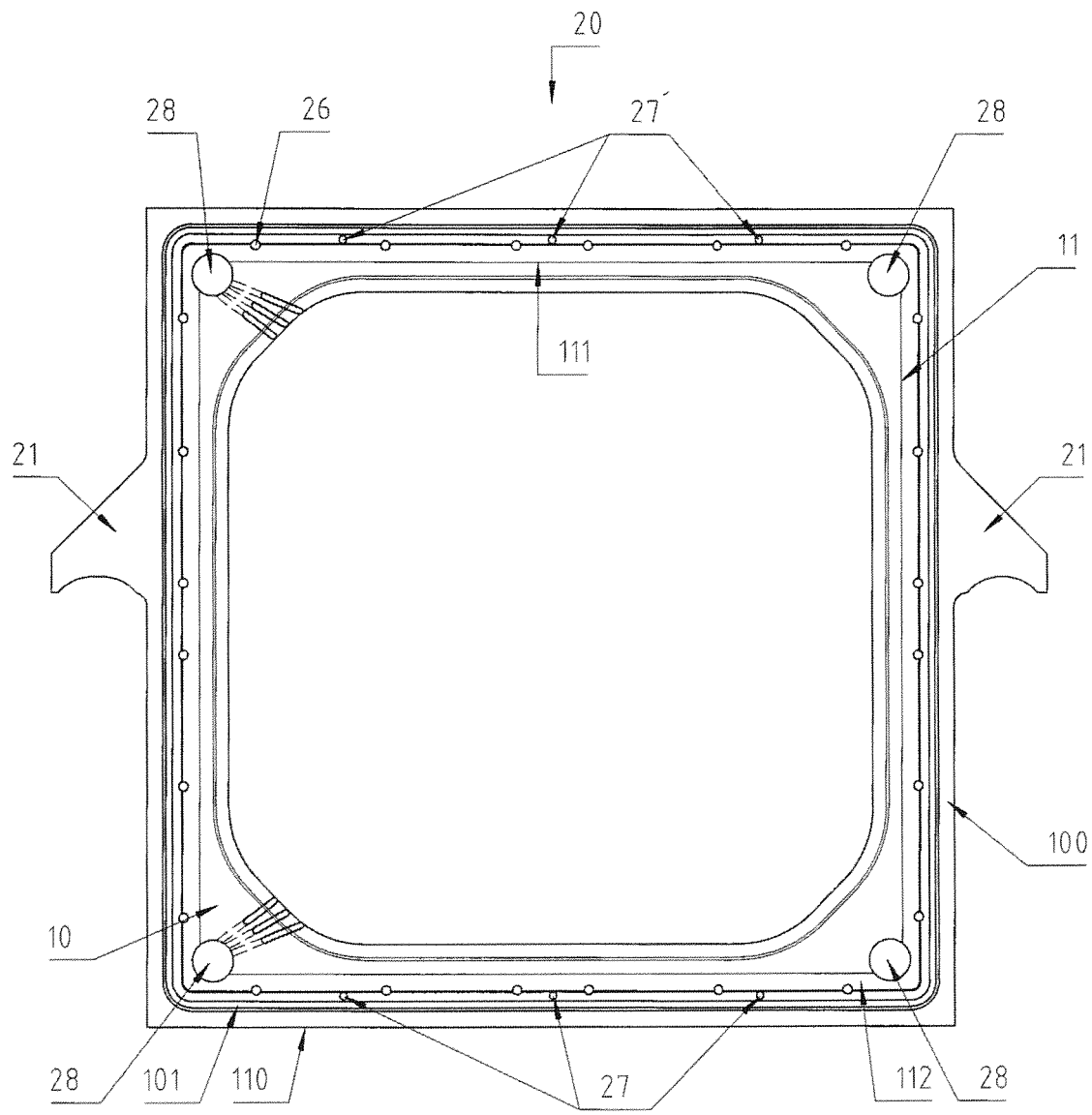
FIG. 2 shows a top view of a frame plate.

The frame plate 20 represented in FIG. 2 is composed of a base body 10 and is made from a material with hardness $H_1$ with an outer circumferential surface 11 and a frame 100 and is made from a material $H_2$ with an outer circumferential surface 110, an inner circumferential surface 111 and two side surfaces 112. The frame 100 surrounds the outer circumferential surface 11 of the base body 10, the outer circumferential surface 11 of the base body 10 being welded to the inner circumferential surface 111 of the frame 100. On each side surface 112 of the frame 100 there is arranged an encircling, closed seal 101. Since FIG. 2 is a top view, only one side surface 112 can be seen.

Figure 5:
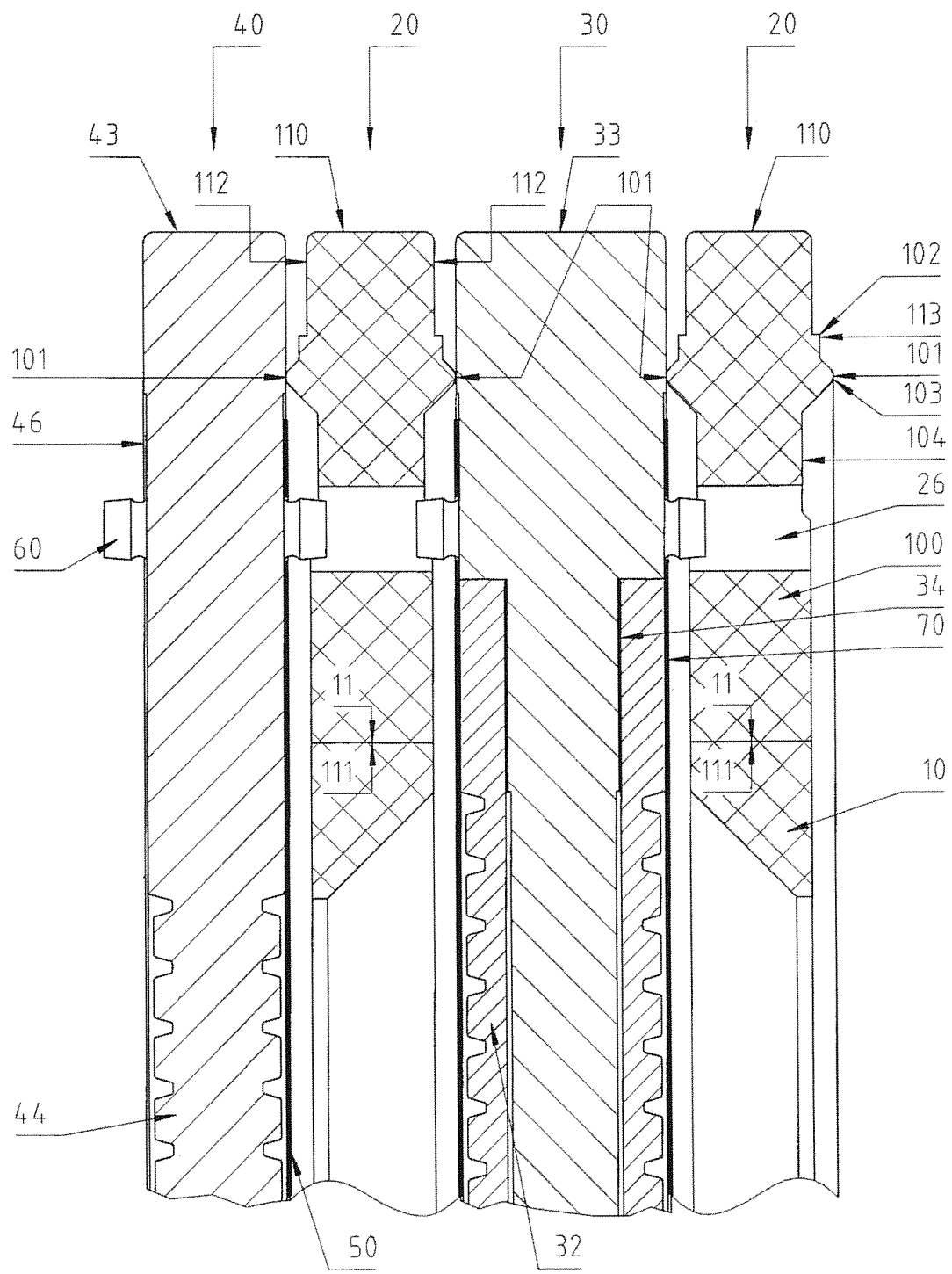
FIG. 5 shows a feature of a plate arrangement in cross section in the opened state of the filter press.

As can be seen in FIG. 5, the seal 101 has a steplike configuration and in the unloaded state which is shown it has a first protrusion 102 and a second protrusion 103, both protrusions 102, 103 bordering on each other and the second protrusion 103 extending beyond the first protrusion 102. The first protrusion 102 lies closer to the outer circumferential surface 110 of the frame 100 than the second protrusion 103 in the sample embodiment shown.

At the inside of the seal 101 there runs a groove 104, which borders directly on the second protrusion 103 and can be milled from the frame material. In the groove 104 are found through boreholes 27, which serve for the supply and drainage of cleaning agent (see FIG. 2, not visible in FIG. 5). The through boreholes 27 are located, in terms of the installation state of the frame 20, in the lower part of the encircling groove 104. In the upper part of the groove 104 are found through boreholes 27', which serve for venting of the chamber region during the cleaning procedure and ensure that the cleaning agent can reach all product-contacting regions.

In the example shown, the frame plate 20 furthermore has boreholes 26 in the inner margin region of the encircling groove 104, which serve for receiving retaining pins 60 of adjacent membrane and filter plates 30, 40, serving for the fastening of filter cloths 50, 70 (see FIG. 5).

For sake of completeness, FIGS. 3 and 4 show a membrane plate 30 and a filter plate 40 which are already known from the prior art and which can be used in conjunction with the frame plate of FIG. 2 in a filter press 1 according to the invention.

FIG. 3 shows a top view of such a membrane plate 30, not showing the filter cloth 70 supported by retaining pins 60. The retaining pins 60 are arranged at a spacing from the outer circumferential surface 33 of the membrane plate 30 and lie substantially in the region of the connection line of the eyelets 38 which are situated in the corner regions of the membrane plate 30. Moreover, there can be seen a membrane 32, which lies in a recess 34. The membrane plate 30 furthermore has an annular groove 36, in which the filter cloth 70 terminates (see also FIG. 5).

FIG. 4 shows a filter plate 40 which is configured in similar manner to the membrane plate 30 and which likewise has retaining elements 60 which are arranged at a spacing from the outer circumferential surface 43 of the filter plate 40 (see also FIG. 5). Here as well there is provided an annular groove 46, in which the filter cloth 50 terminates. The configuration of the annular groove 46 corresponds to that of the annular groove 36. Moreover, eyelets 48 are provided in the corner regions of the filter plate 40. The inner region of the filter plate 40 is provided with knobs 44, on which the filter cloth 50, not shown, is placed.

Figure 6:
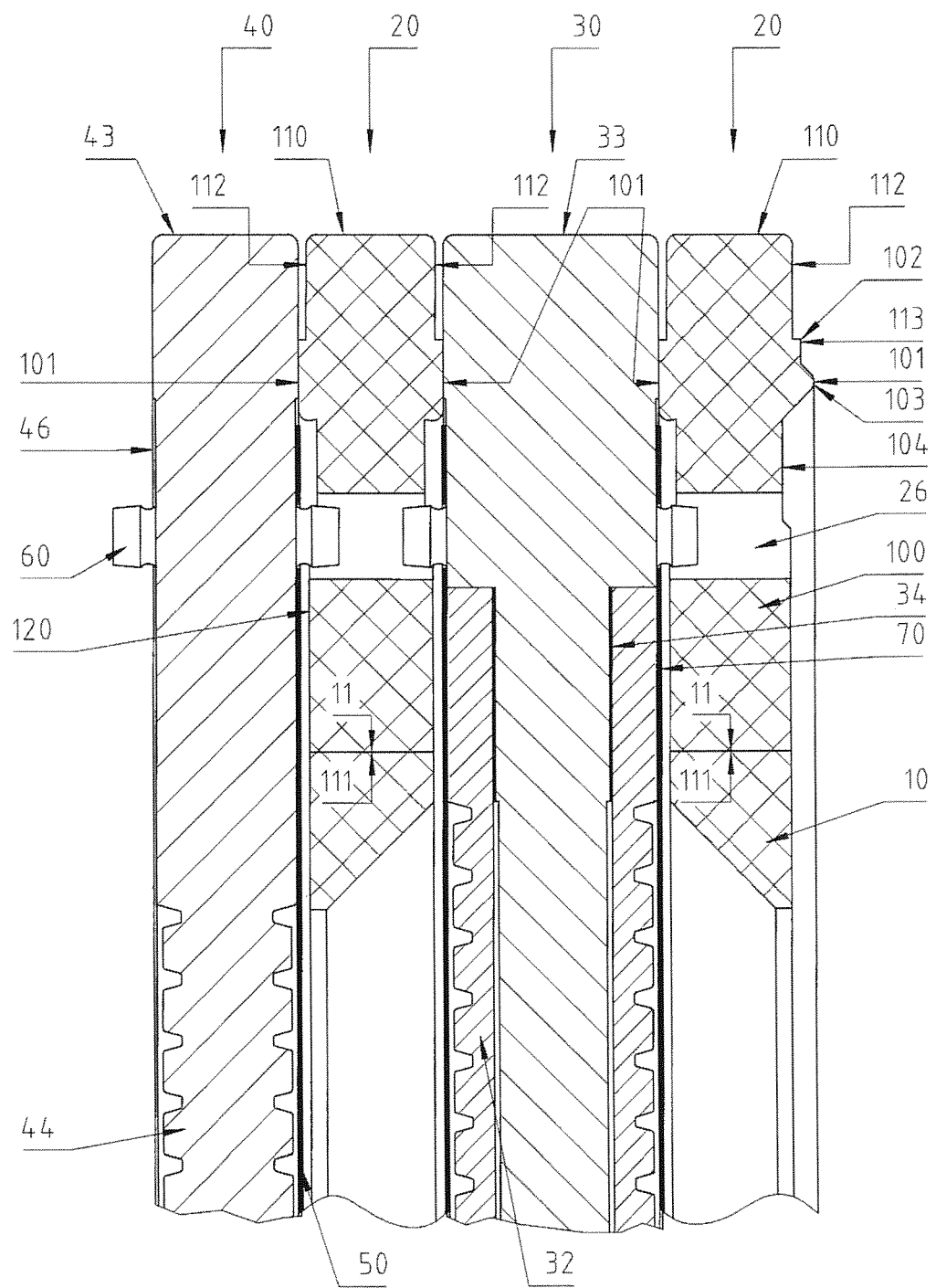
FIG. 6 shows a feature of a plate arrangement in cross section in the cleaning state of the filter press.
Figure 7:
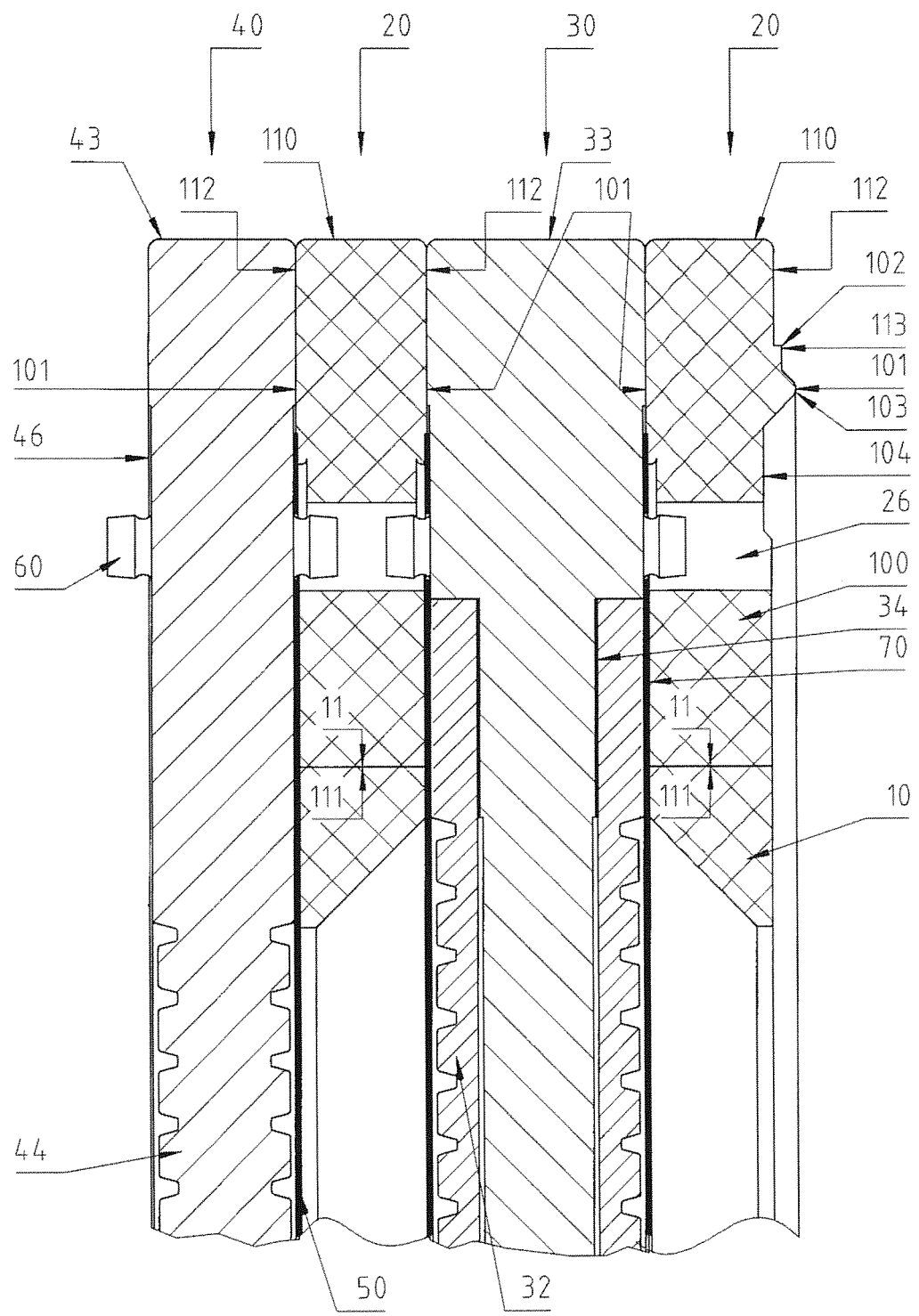
FIG. 7 shows a feature of a plate arrangement in cross section in the filter state of the filter press.

FIGS. 5 to 7 each show a feature of the plate arrangement 9 in different operating states of the filter press 1 and should clarify the mode of operation of the invention.

FIG. 5 shows the plate arrangement 9 with plates 20, 30, 40 in the opened state of the filter press 1, no pressing force being applied to the plates 20, 30, 40.

The plate arrangement 9 has frame plates 20, membrane plates 30 and filter plates 40, with membrane and filter plates 30, 40 alternating and with a frame plate 20 situated between them each time, having a frame with the above described frame 100 and seal 101.

The membrane plate 30 has a membrane 32 on each of its side surfaces, which is covered by a filter cloth 70. The filter cloth 70 is fastened by means of retaining pins 60 in the margin region of the membrane plate 30.

The side surfaces of the filter plate 40 are likewise each fitted with a filter cloth which, as in the case of the membrane plate 30, is fastened by means of retaining pins 60 in the margin region of the filter plate 40.

The frame plate 20 shown in cross section in FIGS. 5 to 7 corresponds to the frame plate 20 of FIG. 2 and therefore comprises the base body 10 and the flexible frame 100. On the side surfaces 112 of the frame 100 are situated the seals 101. The first protrusion 102 of the seal 101 has an abutment surface 113 parallel to the side surface 112. The second protrusion 103 is hump shaped in the example shown.

FIG. 6 shows the plate arrangement 9 in the intermediate position in which the cleaning and sterilization of the plates 20, 30, 40 is performed.

For the cleaning of all product-contacting regions of the plates 20, 30, 40, the plate arrangement 9 is compressed with a pressing force, which typically amounts to between 20 and 70 bar, until the membrane plate 30 and the frame plate 40 lie against the abutment surfaces 113 of the first protrusion 102 of the seals 101. Between the plates 20, 30, 40 are formed gaps 120 with a width of a few mm, into which the sterilization medium can penetrate. The gap width corresponds to the height of the first protrusion 102, which forms an end stop for the neighboring plates and ensures a uniform propagation of the pressing force over the entire plate arrangement 9 thanks to its good resistance to deformation.

FIG. 7 shows a feature of the plate arrangement 9 from FIGS. 5 and 6 in filter mode. The plates are pressed entirely against each other with a large pressing force of around 240 bar. The flexible seal 101 is completely compressed, the displaced sealing material being taken up in the groove 104.

FIG. 8 shows a filter plate 40 with the features according to the invention. The filter plate 40 comprises a base body 10, which is welded by its outer circumferential surface 11 to the inner circumferential surface 111 of the frame 100. The base body 10 consists of a material of hardness $H_1$ while the material of the frame 100 has a hardness $H_2$. Also in this embodiment, $H_2 < H_1$. The retaining pins 60 in this embodiment are part of the base body 10. The design of the seal 101 protruding with respect to the side surface 112 corresponds to the design of the seal 101 of the frame plate 20 in FIG. 5. The seal 101 has a first protrusion 102 and a second protrusion 103, with the second protrusion 103 extending beyond the first protrusion 102. The first protrusion 102 has the parallel abutment surface 113. The groove 104 is situated adjacent to the second protrusion.

FIG. 9 shows a membrane plate 30 with the features according to the invention. The membrane plate 30 has a base body 10 and a frame 100. The retaining pins 60 are likewise part of the base body 10. The base body 10 is welded by its outer circumferential surface 11 to the inner circumferential surface 111 of the frame 100. For the materials of base body 10 and frame 100, the same materials are used as for the base bodies 10 and frames 100 of the filter plate 40 and the frame plate 20. In this embodiment as well, the hardness $H_2$ of the frame 100 is less than the hardness $H_1$ of the base body. On both side surfaces 112 there is arranged a respective seal 101 according to the invention, while the sequence of first protrusion 102 and second protrusion 103 has been interchanged. This means that the first protrusion 102 is arranged on the inside and the second protrusion 103, which extends beyond the protrusion 102, faces the circumferential surface 33. Accordingly, the encircling groove 104 is also arranged between the circumferential surface 33 and the second protrusion 103.

LIST OF REFERENCE NUMBERS

1 Filter press
2 Mobile frame
3a, b Frame plate
4 Support beam
5 Connections
7 Hose
7' Pressurized air port
8 Rod
9 Plate arrangement
10 Base body
11 Outer circumferential surface
20 Frame plate
21 Retaining tab
26 Borehole
27, 27' Through borehole CIP
28 Eyelet
30 Membrane plate
31 Retaining tab
32 Membrane
33 Outer circumferential surface
34 Recess
36 Annular groove
38 Eyelet
40 Filter plate
41 Retaining tab
43 Outer circumferential surface
44 Knobs
46 Annular groove
48 Eyelet
50 Filter cloth
60 Retaining pins
70 Filter cloth
100 Frame
101 Seal
102 First protrusion
103 Second protrusion
104 Groove
110 Outer circumferential surface
111 Inner circumferential surface
112 Side surface
113 Abutment surface
120 Gap
$H_1$ Hardness of the base body 10
$H_2$ Hardness of the frame 100

What is claimed is:

1. A plate for a filter press, comprising:
    a base body, consisting of a first material with a hardness Hi and having an outer circumferential surface,
    a frame arranged on the outer circumferential surface, consisting of a second material with a hardness $H_2$, where $H_2<H_1$,
    wherein the frame has an outer circumferential surface, an inner circumferential surface and two sides surfaces,
    wherein the frame has on at least one of the side surfaces at least one encircling seal protruding outwardly relative to the side surface, wherein the at least one encircling seal and the frame are made from a single piece of one material,
    wherein the encircling seal in the unloaded condition has a first protrusion which passes into a second protrusion, wherein the second protrusion is located further away from the side surface than the first protrusion,
    wherein the frame has at least one through borehole for the supply and drainage of cleaning agent and/or sterilization agent and at least one through borehole for venting, and
    wherein the through boreholes extend from one of the side surfaces of the frame to the other side surface of the frame.

2. The plate as claimed in claim 1, wherein the frame is joined by its inner circumferential surface to the outer circumferential surface of the base body.

3. The plate as claimed in claim 1, wherein the inner circumferential surface of the frame is welded to the outer circumferential surface of the base body.

4. The plate as claimed in claim 1, wherein the frame has a hardness $H_2$ of 90 to 100 shore A.

5. The plate as claimed in claim 1, wherein the frame has a thermoplastic elastomer or consists of the thermoplastic elastomer.

6. The plate as claimed in claim 1, wherein the base body has a hardness $H_1$ of 60 to 80 shore D.

7. The plate as claimed in claim 1, wherein the second protrusion extends beyond the first protrusion.

8. The plate as claimed in claim 1, wherein the first protrusion has an abutment surface oriented parallel to the side surface of the frame.

9. The plate as claimed in claim 1, wherein the first protrusion is arranged closer to the outer circumferential surface of the frame than the second protrusion.

10. The plate as claimed in claim 1, wherein the side surface having the seal has an encircling groove, and the groove is adjacent to the second protrusion.

11. The plate as claimed in claim 1, wherein the plate is a filter plate.

12. The plate as claimed in claim 1, wherein the plate is a membrane plate.

13. The plate as claimed in claim 1, wherein the plate is a frame plate.

14. The plate as claimed in claim 10, wherein the through boreholes are arranged in the encircling groove.

15. A filter press with a plate arrangement, having a plurality of plates arranged parallel to each other, wherein at least every second plate is a plate as claimed claim 1.

16. A method of using a filter press, comprising the steps of: obtaining a filter press as claimed in claim 15; and
    filtering blood plasma or manufacturing pharmaceutical products with the filter press.

17. A method for cleaning the plates of a filter press as claimed in claim 15, involving the following steps:

(a) a first compressing of the plates, wherein only the second protrusion of the seal is compressed,
(b) at least one rinsing procedure with a cleaning, rinsing and/or sterilization medium and
(c) a second compressing of the plates, wherein both the second and also the first protrusion of the seal are entirely compressed.

18. The method as claimed in claim 17 for cleaning the plates of a filter press, wherein the following steps are performed in advance of steps (a), (b) and (c):
(1) sliding apart the plate arrangement,
(2) removal of the filter cake,
(3) removal of the plates and separate cleaning
(4) installing of the cleaned plates.

* * * * *